United States Patent [19]

Franco, III

[11] 4,301,791

[45] Nov. 24, 1981

[54] BODY TRANSFER UNIT

[76] Inventor: Adolph S. Franco, III, 33 Woodland Dr., Waterford, Conn. 06385

[21] Appl. No.: 122,671

[22] Filed: Feb. 19, 1980

[51] Int. Cl.³ .......................... A61F 5/01; A61F 5/37; A61F 13/00
[52] U.S. Cl. .......................... 128/89 R; 128/DIG. 20; 128/DIG. 15; 128/134; 9/330; 5/455
[58] Field of Search .................. 128/24 R, 64, 70, 68, 128/69, 78, DIG. 20, 83, 87 R, 89 R, 298, 299, 402, 134; 9/11 A, 13, 14, 330, 331, 333, 348; 5/81 R, 81 B, 82 R, 440, 441, 442, 449, 455; 27/13, 19, 28

[56] References Cited

U.S. PATENT DOCUMENTS

| | | | |
|---|---|---|---|
| 867,464 | 10/1907 | Abbott | 128/134 |
| 1,113,074 | 10/1914 | Voegeli | 9/330 |
| 2,534,471 | 12/1950 | Norheim | 128/24 R |
| 3,286,707 | 11/1966 | Shafer | 128/24 R |
| 3,382,504 | 5/1968 | Barbosa | 9/330 |
| 3,775,782 | 12/1973 | Rice et al. | 128/DIG. 20 |
| 3,811,433 | 5/1974 | Brachet | 128/84 C |
| 4,014,344 | 3/1977 | Gutierrez | 128/298 |
| 4,024,861 | 5/1977 | Vincent | 128/87 R |
| 4,067,075 | 1/1978 | Leathers et al. | 9/13 |
| 4,139,004 | 2/1979 | Gonzalez, Jr. | 128/402 |

FOREIGN PATENT DOCUMENTS 558711  6/1958  Canada .................. 9/11 A

*Primary Examiner*—Robert W. Michell
*Assistant Examiner*—Arthur S. Rose
*Attorney, Agent, or Firm*—Albert W. Hilburger

[57] ABSTRACT

A body transfer device comprises front and rear inflatable support members which can be selectively joined to completely envelop a person's body. When the support members are inflated, the body is rendered substantially immobile. Openings are provided to accommodate the person's face and to enable access to vital portions of the body, if needed. A reinforcing board can be releasably attached to the rear support member to aid in transporting the person when the device is fully inflated.

10 Claims, 9 Drawing Figures

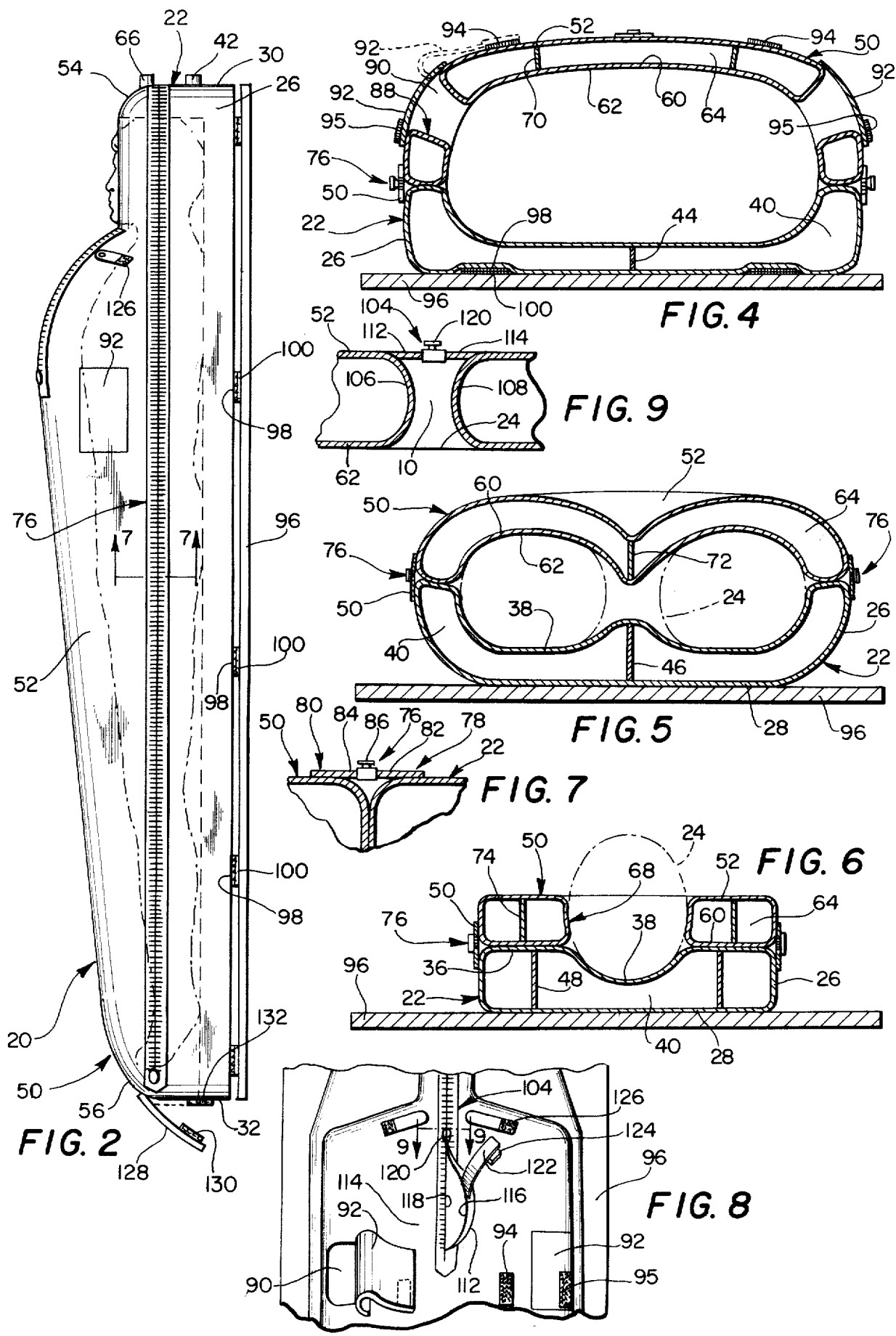

BODY TRANSFER UNIT

BACKGROUND OF THE INVENTION

1. Field of Invention

This invention relates to a new and improved body transfer device for rendering a patient's body substantially immobile pending treatment and while transferring the patient from one location to another.

2. Description of the Prior Art

Over the years, significant strides have been made in devices serving to render portions of a body immobile while transporting them from one location to another. Examples of such devices which have been known to the prior art are British Pat. No. 268 of 1892, U.S. Pat. No. 3,811,433 to Brachet issued May 21, 1974, and U.S. Pat. No. 4,024,861 to Vincent, issued May 24, 1977. In the case of the British patent, the invention resides in a stuffed or air mattress recessed to the shape and form of the body of a patient to be placed thereon. In that instance, the weight of the patient's body serves to maintain the patient in position while being transported from place to place. The patent to Brachet discloses traction apparatus for a prone patient on a stretcher including an inflatable chest belt to immobolize the pelvis of the injured person. In a similar disclosure, the Vincent patent provides a spinal support, particularly for use in first aid treatment of victims having spinal injuries. The spinal support is in the form of an inflatable bag which extends between the top of a victim's head and the lower end of his or her spine, with straps being provided to attach the support to the injured person.

There have also been notable advancements in stretchers and the like, one example of the present state of the art being the U.S. Pat. No. 4,067,075 to Leathers, issued Jan. 10, 1978. The Leathers patent discloses an inflatable stretcher of reinforced construction provided with a plurality of herringbone pattern inflatable compartments and a plurality of integral handles for transportation of a patient. The Leathers stretcher is of lightweight construction and can be easily stored when deflated.

SUMMARY OF THE INVENTION

In some instances, the prior art disclosed complex devices which were expensive to manufacture and maintain; sometimes they were heavy and lacked portability; and none known to the inventor served to immobolize the entire body of the patient. It was with recognition of the need and of the state of the prior art that the present invention was conceived. To this end, the present invention discloses a body transfer device comprising front and rear inflatable support members which can be selectively joined to completely envelop a person's body. When the support members are inflated, the body is rendered substantially immobile. Openings are provided to accommodate the person's face and to enable access to vital portions of the body, if needed. A reinforcing board can be releasably attached to the rear support member to aid in transporting the person when the device is fully inflated.

The present invention, as disclosed, is light, portable, readily usable, employs existing and inexpensive materials, and can be used in conjunction with existing first aid equipment such as stretchers, ambulances, and the like. Becase the present invention is inflatable, it can be easily carried in a rescue vehicle and inflated at such time that its use becomes necessary or desireable. The invention can be employed prior to treatment of patients suffering from a variety of maladies including fractures, heart attacks, electrical shock, burns, head injuries, amputations, hypothermia, and hypovelemia, or in any other situation in which there may be elapsed time before the patient will be treated. The device can even provide restraint for the treatment of psychiatric patients.

The invention is as applicable in water as on land; indeed, because of its inflatable construction, the invention floats such that a patient can be secured, then supported on the water awaiting transportation to a first aid or hospital facility.

Additionally, because the invention does not utilize metallic components in its construction to any significant degree, it permits x-rays to be taken while the patient is in the immobile state. Furthermore, although the present body transfer device substantially encloses the entire body of the patient, it is provided with a proper opening to accommodate the face of the patient and, additionally, one or more openings are provided to enable access to selected parts of the patient's body. As an example, one benefit of the latter construction is that a person encased within the invention could simultaneously be provided with a blood transfusion.

Yet another benefit of the invention is its ability to be selectively provided with a reenforcing board to thereby render further rigidity to the device for greater ease of transporting the patient while maintaining the patient essentially immobile.

Other and further features, objects, advantages, and benefits of the invention will become apparent from the following description taken in conjunction with the following drawings. It is to be understood that both the foregoing general description and the following detailed description are exemplary and explanatory, but are not restrictive of the invention. The accompanying drawings, which are incorporated in and constitute a part of the invention, illustrate one embodiment of the invention, and together with the description, serve to explain the principles of the invention.

BRIEF DESCRIPTION OF THE DRAWINGS

In the drawings:

FIG. 2 is a side elevation view of the invention illustrated in FIG. 1;

FIG. 4 is a cross-section view taken generally along line 4—4 in FIG. 1;

FIG. 5 is a cross-section view taken generally along line 5—5 in FIG. 1;

FIG. 6 is a cross-section view taken generally along line 6—6 in FIG. 1;

FIG. 7 is a detail cross-section view taken generally along line 7—7 in FIG. 2;

FIG. 8 is a detail top plan view illustrating portions of the invention in an open condition; and FIG. 9 is a detail cross-section view taken generally along line 9—9 in FIG. 8.

DESCRIPTION OF THE PREFERRED EMBODIMENT

Figure 1:
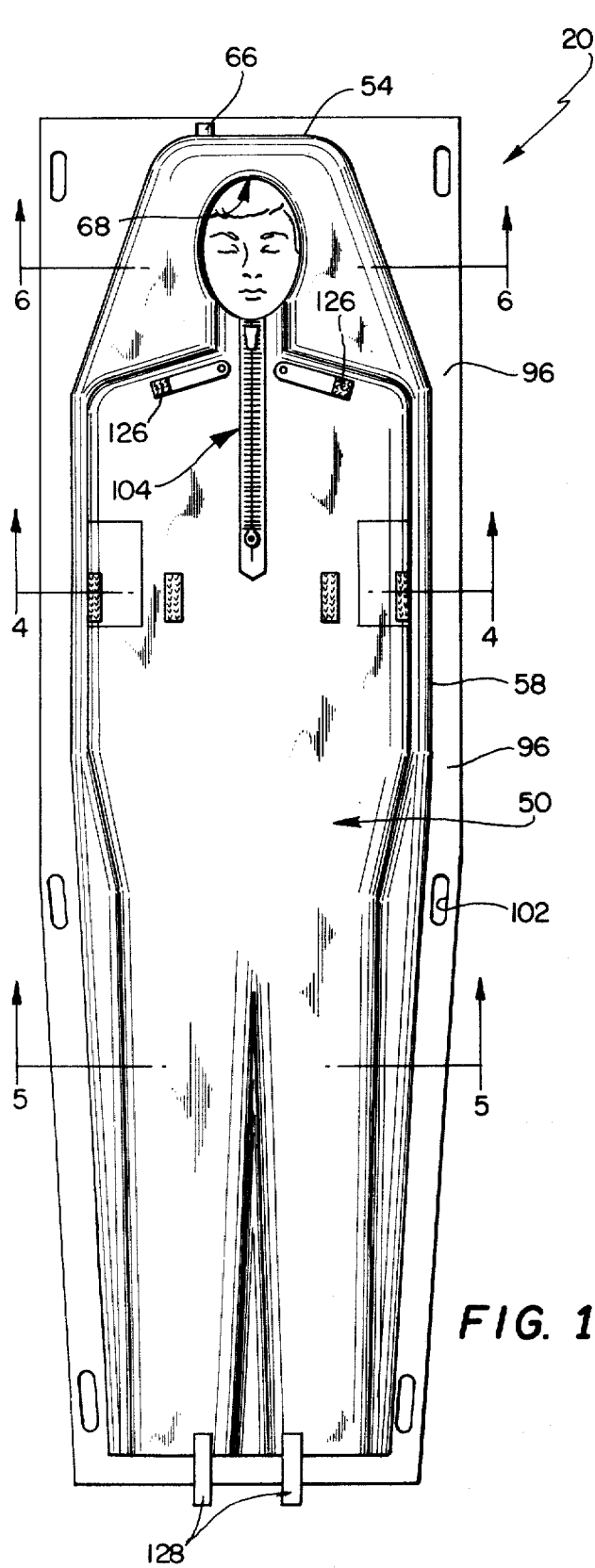
FIG. 1 is a top plan view of the invention in use and containing a person's body.

Refer now to the drawings and initially to FIG. 1 which is generally illustrative of the invention. In FIG. 1, a body transfer device 20 is illustrated in condition for use and containing the body of a person who is to utilize the benefits of the invention (hereinafter "user"). It is readily apparent from FIG. 1 that the body transfer device 20 substantially completely envelops the user's body, only the user's face being left uncovered for reasons including breathing, food intake, and to prevent any possible feeling of claustrophobia. With the body transfer device in the fully inflated condition illustrated, the body is rendered substantially immobile and can be readily transported from one place to another without causing further injury to a person who may already be injured.

In accordance with the invention, the body transfer device 20 comprises a first support member adapted to receive and envelop the entire backside of a user's body, said first support member being inflatable and comprising an outer shell portion including a substantially planar undersurface, a head end, a foot end, and side portions; an inner shell portion integral with and generally coextensive with said outer shell portion and having a first interior surface including a body receiving portion contoured generally to receive the user's body and having depressions to accommodate, respectively, the head and neck, shoulders, arms, torso, legs, and feet of the user, said outer shell portion and said inner shell portion being of unitary construction and defining an airtight cavity therebetween; spacer means within the cavity extending between said outer shell portion and said inner shell portion for providing said inner shell portion with a three-dimensional profile defining the depressions to accommodate the user's body when said first support member is inflated.

Figure 3:
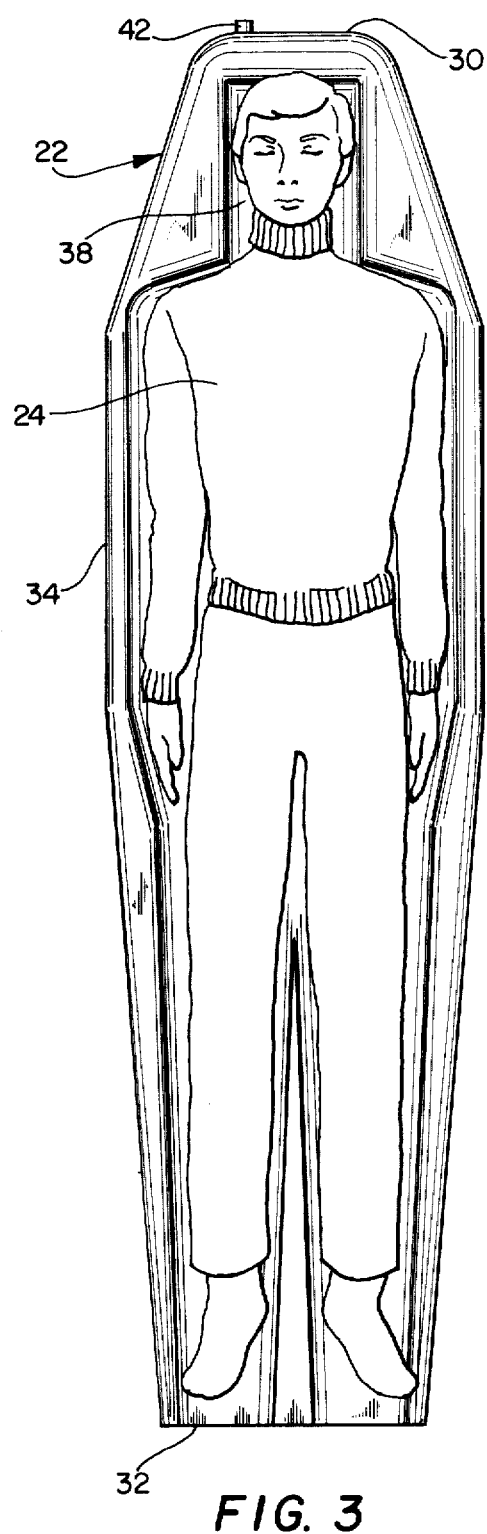
FIG. 3 is a top plan view of a part of the invention, similar to FIG. 1, but with certain parts removed and illustrating the position taken by the body of a person for whose benefit the invention is being used.

As embodied herein, and with particular reference initially to FIGS. 1 and 2, the body transfer device 20 is preferably composed of a rubber-like or plastic material of moderate weight. Polyvinyl chloride having a 19 mil thickness has been found to be an excellent material for the purposes of the present invention, but is only one example of many such materials which may be suited for the purpose, and the scope of the invention should not be restricted to the example provided. Viewing now FIGS. 2 and 3 in particular, a first support member 22 is adapted to receive and envelop the entire backside of a user's body 24, one who may have been injured or become otherwise incapacitated. In some instances, the user would require a supporting surface and may also have to be transported to a medical care or convalescent facility. The first support member 22 is inflatable and, as seen particularly well in FIGS. 4–6, is provided with an outer shell portion 26 including a substantially planar under surface 28 and, for ease of description, a head end 30, a foot end 32, and side portions 34.

As previously recited, the first support member 22 also includes an inner shell portion 36 which is integral with and generally coextensive with the outer shell portion 26 and has a first interior surface 38 which defines a body receiving portion contoured generally to receive the user's body 24. The first interior surface 38 is suitably formed with the necessary depressions to accommodate all the parts of the user's body, from the head down to the feet. Although, for purposes of description, the outer shell portion 26 and the inner shell portion 36 are separately numbered, they are in fact of unitary construction and define an air tight cavity 40 within them. The cavity 40 can be selectively inflated with air or other suitable gas by means of a suitable valve 42. Of course, the valve 42 can also serve to permit deflation of the cavity 40 so that the first support member 22 can be folded up and occupy a minimum amount of space when not in use.

A plurality of spacer means in the form, for example, of strips 44 (FIG. 4), 46 (FIG. 5), and 48 (FIG. 6) which are preferably of the same weight and material as employed in the construction of the support member 22 are seen to extend generally between the under surface 28 and the inner shell portion 36 of the support member. The ends of the strips are suitably fastened, respectively, to the under surface 28 and inner shell portion 36 as by use of suitable adhesive, or by heat sealing, or by ultrasonic welding, or in some other suitable fashion. By properly locating the strips as represented by the reference numerals 44, 46, and 48, and by properly varying their lengths in each instance, the inner shell portion 36 of the support member 22 is thereby provided with a three-dimensional profile suitable for accommodating a user's body 24 when the support member 22 is inflated.

Further in accordance with the invention, a second support member adapted to overlie said first support member and substantially envelop the entire front side of the user's body when placed in said body transfer device, said second support member being inflatable and generally contiguous and coextensive with said first support member comprising an outer shell portion including a generally rounded upper surface, a head end, a foot end, and side portions; an inner shell portion integral with and generally coextensive with said outer shell portion and having a second interior surface which defines a body receiving portion contoured generally to conform to the front side of the user's body, said outer shell portion and said inner shell portion being of unitary construction and defining an airtight cavity therebetween; a face receiving portion adjacent to said head end comprising a continuous surface integral with said outer shell portion and said inner shell portion and extending from said upper surface to said interior surface, said face receiving portion adapted to receive the head of the person therein in a contiguous relationship; spacer means within the cavity extending between said outer shell portion and said inner shell portion for providing said inner shell portion with a three-dimensional profile to accommodate the user's body when said second support member is inflated.

As embodied herein, and with particular reference now to FIGS. 2 and 4–6, a second support member 50 is seen to overlie the first support member 22 whenever the transfer device 20 is called upon to accommodate the body of a person. The support member 50 substantially envelops the entire front side of the user's body 24 when placed in the transfer device 20. As with the first support member 22, the second support member 50 is inflatable and, when applied to the support member 22 is generally contiguous and coextensive with the latter member.

With particular reference to FIGS. 4–6, the second support member 50 is provided with an outer shell portion including a generally rounded upper surface 52, a head end 54, a foot end 56, and side portions 58. The second support member 50 also includes an inner shell portion 60 integral with and generally coextensive with the outer shell portion as already defined and has a second interior surface 62 which defines a body receiving portion contoured generally to conform to the front side of the user's body. The outer shell portion as defined by the upper surface 52, head end 54, foot end 56, and side portions 58, and the inner shell portion 60 are of unitary construction and define an air tight cavity 64 within them. The cavity 64 can be selectively inflated with air or other suitable gas by means of a suitable valve 66. As in the instance of the first support member 22, the valve 66 can also serve to permit deflation of the cavity 64 so that the second support member 50 can occupy a minimum amount of space when not in use and be easily portable.

In actual use, the user's body would be positioned within the first support member 22 on the first interior surface 38, the support member 22 being in the inflated condition. The second support member 50 would likewise be inflated and the second interior surface 62 would be caused to press down upon all the parts of the user's body, from the head down to the feet.

The second support member 50 also includes a face receiving portion 68 which is located adjacent to the head end 54 and comprises a continuous surface integral with the outer shell portion and the inner shell portion and, indeed, extends from the upper surface 52 to the interior surface 62. The face receiving portion 68, as particularly well seen in FIGS. 1 and 6, is adapted to receive the user's head in a contiguous relationship, that is, that when the second support member 50 overlies the body of the person and is inflated, the surfaces defining the face receiving portion press against the sides and top of the user's head and renders the head substantially immobile in the same manner that the entire support member 50 renders the remainder of the body substantially immobile.

The plurality of spacer means in the form, for example, of strips 70 (FIG. 4), 72 (FIG. 5), and 74 (FIG. 6) which are preferably of the same weight and material as employed in the construction of the support member 50 are seen to extend generally between the outer shell portion (unnumbered) and the inner shell portion 60. As in the instance of the strips 44, 46, and 48, the ends of the strips 70, 72, and 74 are suitably fastened, respectively, to the outer shell portion and the inner shell portion 60 as by use of suitable adhesive, or by heat sealing, or by ultrasonic welding, or in some other suitable fashion. Similarly, by properly locating the strips as represented by reference numerals 70, 72, and 74, and by properly varying their lengths in each instance, the inner shell portion 60 of the support member 50 is thereby provided with a three-dimensional profile suitable for enveloping the user's body 24 when the support member 50 is inflated.

Further in accordance with the invention, principal closure means are associated with said first and second support members including first and second band members integral, respectively, with said first and second support members, each of said band members having a generally continuous flap portion extending beyond the outer periphery of its said respective support member, said band members being positioned in a contiguous relationship when said second support member overlies said first support member in a generally contiguous and coextensive relationship, and fastener means for releasably joining said flap portions of said first and second band members to thereby substantially enclose and rigidly maintain the user's body between said first and second support members when said first and second support members are substantially fully inflated.

As embodied herein, with particular reference now to FIG. 7, a principal closure means 76 is provided to join the first and second support members, 22 and 50, respectively, when the user's body is substantially enclosed therebetween. When this occurs, the body is rigidly maintained between the support members, rendered substantially immobile and therefore not subject to any additional harm or injury. To this end, the closure means 76 includes first and second band members, 78 and 80, integral, respectively, with the first and second support members, 22 and 50. The band members may be molded with their respective support members, or they may be attached in any suitable fashion to assure that they will remain fixed to the support member. As described previously with respect to the spacing strips, such fastening may be achieved by means of suitable adhesive, or by heat sealing, or by ultrasonic welding, or in some other suitable fashion. In any event, each of the band members 78 and 80 has a generally continuous flap portion, 82 and 84, respectively, which extends beyond the outer periphery of its said respective support member. The band members 78 and 80 assume a contiguous relationship when the second support member 50 overlies the first support member 22 (see especially FIGS. 4–6) in a generally contiguous and coextensive relationship. Thereupon, fastener means 86 of any suitable construction are suitably bonded to the flap portions 82 and 84. The fastener means 86 are employed for releasably joining the flap portions 82 and 84. In this manner, the support members 22 and 50 are held together in a unitary fashion and substantially envelop the body and render it immobile when they are in a fully inflated condition. It will be appreciated that the fastener means 86 may be of any suitable construction as, for example, the snap variety, or may take the form of a zipper (as illustrated), or other continuous closure device commonly available and sold in commerce under the trademark "zip-loc".

In accordance with the invention, the body transfer device is generally as previously described but modified to the extent that said second support member includes port means spaced from said face receiving portion and defining an opening enabling access to regions within said first and second support members from regions external thereof, said port means including a continuous surface integral with said outer shell portion and said inner shell portion and extending from said upper surface to said interior surface.

As embodied herein, with particular reference now to FIGS. 4 and 8, port means 88 are illustrated as being spaced from the face receiving portion 68 and include a continuous surface integral with the inner shell portion 60 and the outer shell portion (unnumbered) and extending from the upper surface 52 to the interior surface 62. In this manner, an opening 90 is defined such that access is obtainable to the user's body for such purposes as blood transfusions, taking blood pressure, and injections of medicants. In practice, it may be desireable to provide a pair of port means 88 (see FIGS. 4 and 8) so as to permit access to each of the user's arms. Of course, additional numbers of port means 88 may be employed or they may be otherwise located as desired.

In accordance with the invention, the body transfer device 20 is generally as previously described but modified to the extent that it includes cover means releasably applicable to said second support member for selectively sealing said port means and preventing access to regions within said first and second support members from regions external thereof and, further, wherein said cover means includes a flexible flap fixed at one location to said outer shell portion adjacent to said port means and movable between an open position generally removed from the opening to a closed position generally overlying the opening, and first and second adherent means on said upper surface and on said flap, respectively, said first and second adherent means being mutually engageable for releasably fixing said flap to said outer shell portion.

As embodied herein, with continuing reference to FIGS. 4 and 8, a cover is shown in the form of a flexible flap 92 which may selectively overlie the opening 90 to thereby seal the port means 88 and prevent access to the body from regions external of the transfer device 20. It might be preferable that the flap be of the same weight and material as employed in the construction of the support member 50 and, at one end, may be suitably fastened, to the support member, adjacent to the opening 90, as by use of suitable adhesive, or by heat sealing, or by ultrasonic welding, or in some other suitable fashion. The flap 92 is movable between an open position generally removed from the opening 90 as indicated in phantom in FIG. 4, to a closed position generally overlying the opening 90 as indicated by solid lines in that figure. In any event, first adherent means 94 of any suitable nature such as snaps, adhesive, or other devices such as those commonly available and sold in commerce under the trademark "Velcro" are suitably provided in an integral manner on the upper surface 52 at a location spaced from the opening 90 and in position to receive a second mating adherent means 95 integral with the outer surface of the flap 92 so as to hold the flap in an open position if desired. Although no such adherent means is illustrated for maintaining the flap 92 in a closed position overlying the opening 90, the provision of such an expedient is deemed within the scope of the present invention.

In accordance with the invention, the body transfer device is generally as previously described but modified to the extent that it includes a generally rigid planar reinforcing member and third and fourth adherent means on said under surface and on said reinforcing member, respectively, said third and fourth adherent means being mutually engageable for releasably fixing said reinforcing member to said planar under surface of said first support member.

As embodied herein, with particular reference to FIGS. 1, 2, and 4-6, it has been found desireable to employ a reinforcing member 96 in the form of a sheet of plywood or other such strong and solid, but preferably lightweight, material to be placed beneath the support member 22, particularly when it is desired to move the user's body any appreciable distance. In keeping with this construction, third adherent means 98 are provided integral with the planar under surface 28 of the support member 22. Fourth adherent means 100, so positioned as to mate with the adherent means 98, are provided integral with the reinforcing member 96. Thus, when the support member 22 is placed onto the reinforcing member 96 and properly positioned, the third and fourth adherent means are mutually engageable for releasably fixing the support member 22 to the reinforcing member. As seen in FIG. 1, the reinforcing member 96 may be provided with openings 102 at spaced locations about its periphery to serve as grips or handholds for greater ease of transporting the transfer device 20.

In accordance with the invention, the body transfer device is generally as previously described but modified to the extent that it is provided with primary access means including a pair of juxtaposed surfaces which communicate with said face receiving portion and extend from said upper surface to said interior surface and which extend in length from said face receiving portion toward said foot end and terminate at a location intermediate said head end and said foot end, said juxtaposed surfaces being spaced apart to define an opening enabling access to regions within said first and second support members from regions external thereof; first and second flexible sheet members integral with said upper surface and generally coplanar therewith positioned to generally overlie the opening defined by said juxtaposed surfaces, each of said sheet members terminating at an edge, said sheet members being movable between a closed position whereat said edges generally face each other and are in a contiguous relationship and an open position whereat said edges are spaced apart; and secondary closure means on said sheet members adjacent their respective said edges for selectively joining said sheet members together to selected stations along the length of said sheet members.

As embodied herein, with particular reference now to FIGS. 8 and 9, a primary access means 104 will now be described which enables the support member 50 to be snugly applied to the person's body. Additionally, it can serve to enable access to the chest regions of the person's body, for example, for purposes of heart massage. The primary access means 104 is defined by a pair of juxtaposed 106 and 108 which communicate with the face receiving portion 68 and extend, from top to bottom, from the upper surface 52 to the interior surface 62. In length, the primary access means 104 extends from the face receiving portion 68 towards the foot end 56 and terminates at a location intermediate the head end 54 and the foot end 56. The juxtaposed surfaces 106 and 108 are spaced apart (see FIG. 9) so as to define an opening 110 which enables access to regions within the interior defined by the support members 22 and 50, that is, where the user's body is positioned.

With continued reference to FIGS. 8 and 9, a pair of flexible sheet members 112 and 114, integral with the upper surface 52 are positioned to generally overlie the opening 110, each terminating at an edge, 116 and 118, respectively (FIG. 8). It will be appreciated that the sheet members 112 and 114 may be molded in an integral fashion with the upper surface 52 or they may be added to the upper surface at a later stage in the manufacture of the body transfer device and attached in any suitable manner, including those methods referred to above. Similarly, the sheet members 112 and 114 are preferably of the same weight and material as employed in the construction of the support members 22 ad 50 although, again, that is not a requirement of the invention.

The sheet members 112 and 114 are movable between a closed position and an open position. In the closed position, the edges 116 and 118 generally face each other and are in a contiguous relationship. In the open position (FIG. 8), the edges 116 and 118 are spaced apart thereby enabling access to the opening 110. Secondary closure means 120 is provided to join the edges 116 and 118 and thereby the sheet members 112 and 114 together at selected stations along the length of the sheet members. It will be appreciated that the closure means 120 may be of any suitable type. For example, it may be a zipper (as illustrated) or other continuous closure device commonly available and sold in commerce with the trademark "zip-loc", either being operable to provide closure to an infinite number of locations along the lengths of the edges 116 and 118. Alternatively, it may be a fastener of the snap variety which is operable to provide closure to a finite number of such locations.

In accordance with the invention, the body transfer device is generally as previously described but further modified to the extent that the primary access means includes a tab member integral with one of said sheets extending beyond its respective said edge, fifth adherent means on said tab member, sixth adherent means integral with said upper surface at a location spaced from said edge, said fifth and sixth adherent means being mutually engageable for releasably holding said one of said sheets in an open position.

As embodied herein, with continuing reference to FIG. 8, the sheet member 112 may be provided with an integral tab member 122 which can extend beyond the edge 116 when the closure means 120 is operated to permit separation of the edges 116 and 118. In order to releasably hold the sheet member 112 open, that is, such that the edge 116 is separated from the edge 118, suitable fifth adherent means 124 is provided on the tab member 122 and, similarly, sixth adherent means 126 is suitably provided on the upper surface 52 so as to be mutually engageable. Although the adherent means 124 and 126 are illustrated as those devices commonly available and sold in commerce under the trademark "Velcro", it will be understood, as previously, that any other suitable means may be employed and still be within the scope.

In accordance with the invention, the body transfer device 20 is generally as previously described including a locking member fixed at one end to said first support member at said foot end and having a free end distant from said first support member, said locking member movable between an open position whereat said free end is spaced from said foot end in a direction away from said head end and a closed position whereat said locking member is generally contiguous with said foot end and overlies said principal closure means; and seventh and eighth adherent means on said foot end of said second support member and on said locking member adjacent said free end, respectively, said seventh and eighth adherent means being mutually engageable for releasably holding said locking member in the closed position.

As embodied herein, with particular reference now to FIGS. 1 and 2, at least one locking member 128 is provided for the purpose of supplementing the principal closure means 76 in the region of the foot end of the body transfer device 20. FIG. 1 illustrates two such locking members being used for reasons of added strength. In some instances, an injured person may experience a substantial degree of pain and be difficult to control, especially in regard to his legs and feet. The locking member 128 serves as an aid to reenforce the foot end of the device 20 to prevent the person from kicking and thus tearing the closure means 76 apart.

To this end, the locking member 128 is preferably composed of the same material utilized in the construction of the remainder of the device 20. As such, each locking member is substantially in the form of a strip of material fixed to the upper surface 52 of the support member 50 adjacent its foot end 56. The locking member 128 may be molded integral with the support member 50 or it may be provided separately and applied to the support member 50 at a later stage of its construction. In the latter instance, the locking member may be applied in any suitable fashion, including the use of adhesive, or by heat sealing, or by ultrasonic welding. As illustrated, the locking member 128 has a free end distant from the support member 50 and is movable between an open position spaced from the foot end of the device 20 and extending in a direction away from the head end (see FIG. 2), and a closed position at which the locking member is generally contiguous with the foot end and overlies the principal closure means 76 (see FIG. 2). Seventh adherent means 130 and eighth adherent means 132 are fixed, respectively, on the locking member 128 and on the foot end 32 of the support member 22 and are mutually engageable for releasably holding the locking member 128 in the closed position indicated in phantom in FIG. 2. Although the adherent means 130 and 132 are illustrated as being those devices commonly available and sold in commerce under the trademark "Velcro", any other suitable means may be employed.

The invention in its broader aspects, is not limited to the specific details shown and described; departures may be made from such details without departing from the principals of the invention and without sacrificing its chief advantages.

What is claimed is:

1. A body transfer device comprising:
(A) a first support member adapted to receive and envelop the entire backside of a user's body, said first support member being inflatable and comprising:
  (1) an outer shell portion including a substantially planar undersurface, a head end, a foot end, and side portions;
  (2) an inner shell portion integral with and generally coextensive with said outer shell portion and having a first interior surface including a body receiving portion contoured generally to receive the user's body and having depressions to accommodate, respectively, the head and neck, shoulders, arms, torso, legs, and feet of the user, said outer shell portion and said inner shell portion being of unitary construction and defining an airtight cavity therebetween;
  (3) spacer means within the cavity extending between said outer shell portion and said inner shell portion for providing said inner shell portion with a three-dimensional profile defining the depressions to accommodate the user's body when said first support member is inflated; and
(B) a second support member adapted to overlie said first support member and substantially envelop the entire front side of the user's body when placed in said body transfer device, said second support member being inflatable and generally contiguous and coextensive with said first support member and comprising:
  (1) an outer shell portion including a generally rounded upper surface, a head end, a foot end, and side portions;
  (2) an inner shell portion integral with and generally coextensive with said outer shell portion and having a second interior surface which defines a body receiving portion contoured generally to conform to the front side of the user's body, said outer shell portion and said inner shell portion being of unitary construction and defining an airtight cavity therebetween;

(3) a face receiving portion adjacent to said head end comprising a continuous surface integral with said outer shell portion and said inner shell portion and extending from said upper surface to said interior surface, said face receiving portion adapted to receive the head of the user therein in a contiguous relationship;

(4) spacer means within the cavity extending between said outer shell portion and said inner shell portion for providing said inner shell portion with a three-dimensional profile to accommodate the user's body when said second support member is inflated; and (C) principal closure means associated with said first and second support members including first and second band members integral, respectively, with said first and second support members, each of said band members having a generally continuous flap portion extending beyond the outer periphery of its said respective support member, said band members being positioned in a contiguous relationship when said second support member overlies said first support member in a generally contiguous and coextensive relationship, and fastener means for releasably joining said flap portions of said first and second band members to thereby substantially enclose and rigidly maintain the user's body between said first and second support members when said first and second support members are substantially fully inflated.

2. A body transfer device as set forth in claim 1 wherein said second support member includes port means spaced from said face receiving portion and defining an opening enabling access to regions within said first and second support members from regions external thereof.

3. A body transfer device as set forth in claim 2 wherein said port means includes a continuous surface integral with said outer shell portion and said inner shell portion and extending from said upper surface to said interior surface.

4. A body transfer device as set forth in claim 3 including cover means releasably applicable to said second support member for selectively sealing said port means and preventing access to regions within said first and second support members from regions external thereof.

5. A body transfer device as set forth in claim 4 wherein said cover means includes a flexible flap fixed at one location to said outer shell portion adjacent to said port means and movable between an open position generally removed from the opening to a closed position generally overlying the opening, and first and second adherent means on said upper surface and on said flap, respectively, said first and second adherent means being mutually engageable for releasably fixing said flap to said outer shell portion.

6. A body transfer device as set forth in claim 1 including a generally rigid planar reinforcing member and third and fourth adherent means on said under surface and on said reinforcing member, respectively, said third and fourth adherent means being mutually engageable for releasably fixing said reinforcing member to said planar under surface of said first support member.

7. A body transfer device as set forth in claim 1 including first valve means for inflating said first support member and second valve means for inflating said second support member.

8. A body transfer device as set forth in claim 1 provided with primary access means including a pair of juxtaposed surfaces which communicate with said face receiving portion and extend from said upper surface to said interior surface and which extend in length from said face receiving portion toward said foot end and terminate at a location intermediate said head end and said foot end, said juxtaposed surfaces being spaced apart to define an opening enabling access to regions within said first and second support members from regions external thereof; first and second flexible sheet members integral with said upper surface and generally coplanar therewith positioned to generally overlie the opening defined by said juxtaposed surfaces, each of said sheet members terminating at an edge, said sheet members being movable between a closed position whereat said edges generally face each other and are in a contiguous relationship and an open position whereat said edges are spaced apart; and secondary closure means on said sheet members adjacent their respective said edges for selectively joining said sheet members together to selected stations along the length of said sheet members.

9. A body transfer device as set forth in claim 8 including a tab member integral with one of said sheets and extending beyond its respective said edge, fifth adherent means on said tab member, sixth adherent means integral with said upper surface at a location spaced from said edge, said fifth and sixth adherent means being mutually engageable for releasably holding said one of said sheets in an open position.

10. A body transfer device as set forth in claim 1 including a locking member fixed at one end to said first support member at said foot end and having a free end distant from said first support member, said locking member movable between an open position whereat said free end is spaced from said foot end in a direction away from said head end and a closed position whereat said locking member is generally contiguous with said foot end and overlies said principal closure means; and seventh and eighth adherent means on said foot end of said second support member and on said locking member adjacent said free end, respectively, said seventh and eighth adherent means being mutually engageable for releasably holding said locking member in the closed position.

* * * * *